United States Patent [19]

Bialek et al.

[11] Patent Number: 4,568,776

[45] Date of Patent: Feb. 4, 1986

[54] PROCESS FOR PURIFYING 2,6-XYLENOL

[75] Inventors: Jerzy Bialek; Marek Plesnar; Janina Werle; Jan Bialy, all of Warsaw, Poland

[73] Assignee: Enichimica S.p.A., Milan, Italy

[21] Appl. No.: 677,232

[22] Filed: Dec. 3, 1984

[30] Foreign Application Priority Data

Dec. 5, 1983 [IT] Italy .............................. 24025 A/83

[51] Int. Cl.$^4$ ...................... C07C 37/84; C07C 37/68
[52] U.S. Cl. ................................................... 568/749
[58] Field of Search ............................... 568/749, 750

[56] References Cited

U.S. PATENT DOCUMENTS 3,337,641  8/1967  Bussink ............................... 568/750
3,337,642  8/1967  Hoefs et al. ......................... 568/750
3,598,873  8/1971  Bloch .................................. 568/749
3,646,006  2/1972  Lord ................................... 568/749

Primary Examiner—Werren B. Lone
Attorney, Agent, or Firm—Hedman, Gibson, Costigan & Hoare

[57] ABSTRACT

A raw 2,6-xylenol product is purified by melting it, then slowly and uniformly cooling it until at least 60 to 100% is crystallized, with the greater concentration of the impurities being present nearer the surface of the resulting crystals, gradually heating the crystalline solid mass to an elevated temperature no higher than by 0.1° to 5° C. below the solidification temperature of 2,6-xylenol to cause only surface melting of the crystals, thus yielding a molten liquid phase and a solid crystalline phase, the solid phase containing 2,6-xylenol in greater purity than the molten phase.

7 Claims, No Drawings

PROCESS FOR PURIFYING 2,6-XYLENOL

FIELD OF THE INVENTION

The present invention relates to the purification of raw 2,6-xylenol, by means of a melting/crystallizing process carried out in the absence of solvents or thinners.

BACKGROUND OF THE INVENTION 2,6-Xylenol is the starting material for the production of polyphenyleneoxide, a valuable polymer used in the art for several applications.

The limited availability of 2,6-xylenol deriving from sources such as the heavy fractions from the distillation of coal, and the problems related to the separation from such sources of 2,6-xylenol at a suitable purity, have promoted the development of processes for the chemical synthesis of 2,6-xylenol. Presently, 2,6-xylenol is produced nearly exclusively by the catalytic methylation of phenol with methanol. In this reaction, together with the desired product 2,6-xylenol, also not negligible quantities are formed of cresols and xylenol isomers of 2,6-xylenol. In the reaction mixture also unconverted reactants, water and several byproducts are present. By separating such a reaction mixture by distillation and rectifying, it is possible to obtain a 2,6-xylenol with a purity of about 95-98%.

However, in the production of polyphenylene oxide by the oxidative polymerization of 2,6-xylenol, a very pure 2,6-xylenol is required, in any case with a purity higher then 99%. Thus, 2,6-xylenol obtained by chemical synthesis undergoes, according to the art known, purification processes, by means of crystallization, mainly from solvents. Selective solvents used for this purpose are, e.g., aliphatic organic acids and water-/ethylene glycol mixtures.

However, the purification of raw 2,6-xylenol on the basis of the crystallization from solvent is generally a complex and also expensive process, due to the need of recovering and regenerating the solvent used for this purpose.

In the disclosure of the French Pat. No. 1.583.244, a process is disclosed for the purification of raw 2,6-xylenol, which consists essentially in heating said solid raw 2,6-xylenol, slowly and gradually, so as to cause only a partial melting of it. In this way, a molten liquid fraction of raw 2,6-xylenol is separated, which is richer in impurity than the fraction which did not undergo the melting.

Such a way of operation, if it on one hand eliminates the drawbacks arising from the use of the solvents, on the other hand does not allow a purified 2,6-xylenol to be obtained at a purity level as high as desirable.

DESCRIPTION OF THE INVENTION

The present invention is based on the observation that a slow and uniform cooling of molten raw 2,6-xylenol allows 2,6-xylenol crystals to be obtained, which are richer in impurities in correspondence of the surface and of surface layers of the same crystals. This allows an easier and more complete withdrawal of the impurities by the melting on the surface of the so obtained crystals, and after all makes it possible to obtain 2,6-xylenol with unusually high purity.

Accordingly, the instant invention relates to the purification of raw 2,6-xylenol by means of a process comprising the following steps carried out in succession:
(a) melting of raw 2,6-xylenol;
(b) slow and uniform cooling of said raw 2,6-xylenol, at a rate of from 0.1° to 10° C./hour, until at least from 60 to 100% of the mass is separated as a crystallized solid;
(c) gradual heating of said crystallized solid, after having separated the possibly remaining liquid molten fraction, in a time of from 1 to 12 hours, up to a highest temperature value lower by from 0.1° to 5° C. than the solidification temperature of 2,6-xylenol, to cause the melting on the surface of said crystals;
(d) separation of the molten liquid fraction so obtained and recovery of solid 2,6-xylenol.

Raw 2,6-xylenol, which is submitted to the purification process according to the present invention, is the technical product, outcoming from the processes of synthesis of it, from phenol and methanol, which shows a content of about 95-98% of 2,6-xylenol, and which contains impurities such as o-cresol, p-cresol, 2,4-xylenol and 2,5-xylenol.

According to the present invention, such a raw 2,6-xylenol is caused to melt, generally at a temperature of the order of from 43° to 45° C. (step a of the process) and is then cooled at a slow and uniform cooling rate of from 0.1° to 10° C./hour, and preferably of from 1° to 2° C./hour, until from 60 to 80%, and preferably 80% about of the mass is separated as crystallized solid (step b of the process). By operating as described, the conditions are created which favor the growth of the crystals, and under which mainly single crystals are obtained, with their surfaces being enriched to impurities, the successful performance being in this way made possible of purification treatments.

According to the process of the present invention, said crystals, after the separation of the liquid molten fraction in the case of partial solidification, are submitted to a gradual heating, in a time of from 1 to 12 hours, up to a maximum temperature value which is lower by 0.1° to 5° C. than the solidification temperature of 2,6-xylenol, with consequent superficial melting of the crystals (step c of the process).

In this step of the process, the molten liquid fraction can be withdrawn either in a continuous way, or batchwise, as a single fraction, or as a plurality of fractions with different impurity contents, and said separated fractions can be recycled to the purification process, after possible preliminary treatments, e.g., a rectifying treatment.

In any case purified crystalline 2,6-xylenol remains as a residue, with a purity generally higher than 99%, and even as high as 99.9%, which is recovered (step d of the process).

The process according to the present invention can be carried out in equipment of the tube nest type, in which inside the tubes the treatments are carried out of solidification/melting of 2,6-xylenol, and externally to the tubes a fluid circulates with controlled temperature.

The following Experimental Examples are illustrative and non limitative of the invention.

EXAMPLE 1

Raw 2,6-xylenol (content of 2,6 xylenol 95.0% by weight, of o-cresol 4.9% by weight, other impurities 0.1% by weight), is submitted to a purification treatment inside the tubes of a tube crystallizer, having the structure of a heat exchanger.

The crystallizer consists of a set of vertical tubes, of length of 6 meters and diameter of 67 mm, welded to the upper and lower end plates of the equipment.

The inlet valve for feeding in the raw 2,6-xylenol is positioned atop, and the drain (discharge) valve is positioned at the bottom of the equipment. The bottom valve is connected, through pipings, to collecting tanks of purified 2,6-xylenol and of the fractions of contaminated 2,6-xylenol.

The crystallizer is moreover provided with a lining, so that the products can be heated or cooled by means of a fluid means circulating within the space surrounding the tubes. To such purpose, the crystallizer is connected with a heat exchanger in which the temperature is controlled of water sent to the crystallizer through a circulation pump.

After the crystallizer has been heated to about 43° C. by means of the water circulating outside the tubes, raw 2,6-xylenol is introduced inside the tubes of the crystallizer. The cooling is then started, with a constant cooling rate of 2° C. per hour, until the thermocouple positioned in the centre of the vertical axis of tube set shows a temperature of 30° C.

At this time, the discharge valve on the bottom of the crystallizer is opened, and the solidified mass inside the tubes is heated, by increasing the temperature of circulating water at a rate of 2° C./hour for four hours. During this time period a liquid fraction is collected of contaminated 2,6-xylenol (fraction 1). The temperature of circulating water is then gradually increased up to 42° C. and is held at this value for the next 4 hours. During this time period, another liquid fraction is collected of contaminated 2,6-xylenol (fraction 2). The temperature of circulating water is finally raised at 55° C., so as to melt the residual solid inside the tubes and to discharge purified 2,6-xylenol (end product).

In Table 1 the results are shown of the Example described hereinabove.

TABLE 1

| Fraction | Parts by weight | 2,6-xylenol (% by weight) | o-cresol (% by weight) | Solidification temp. (°C.) |
| --- | --- | --- | --- | --- |
| Raw material | 100 | 95.0 | 4.9 | 41.4 |
| Fraction 1 | 31 | 87.8 | 12.2 | 35.9 |
| Fraction 2 | 9 | 95.5 | 4.5 | 41.7 |
| End product | 60 | 99.1 | 0.9 | 44.5 |

EXAMPLE 2

The process is carried out as described in Example 1, initially cooling the mass of liquid raw 2,6-xylenol (containing 97.8 by weight of 2,6-xylenol and 2.2 by weight of o-cresol), at the rate of 1° C./hour, until a temperature of 32° C. is reached at the center of the vertical axis of the tube nest.

The discharge valve is then opened and the temperature of circulation water is gradually raised to 42.5° C., and is maintained at this value for the next 6 hours. During this time period, a liquid fraction is collected of contaminated 2,6-xylenol (fraction 1). Successively, the temperature of circulation water is gradually increased up to 44.5° C., and is kept at this value for the next 6 hours. During this time period, another liquid fraction is collected of contaminated 2,6-xylenol (fraction 2).

The temperature of water is finally raised, so as to melt the solid residue inside the tubes, and to discharge the purified 2,6-xylenol (end product).

In Table 2 the results are shown of the Example described above.

TABLE 2

| Fraction | Parts by weight | 2,6-xylenol (% by weight) | o-cresol (% by weight) | Solidification temp. (°C.) |
| --- | --- | --- | --- | --- |
| Raw material | 100 | 97.8 | 2.2 | 43.5 |
| Fraction 1 | 28 | 94.8 | 5.2 | 41.8 |
| Fraction 2 | 19 | 98.8 | 2.0 | 43.6 |
| End product | 53 | 99.5 | 0.4 | 45.1 |

EXAMPLE 3

The process is carried out as described in Example 1, introducing inside the tubes of the crystallizer raw 2,6-xylenol (containing 98.3% by weight of 2,6-xylenol, 1.1% by weight of o-cresol, and 0.5% by weight of 2,4- and 2,5-xylenol).

When the temperature inside the crystallizer is stabilized at 45° C., the mass is gradually cooled at the rate of 1° C./hour, until the temperature of 40° C. is reached, at the center of the vertical axis of tube nest. At this time, the bottom valve is opened, and the fraction 1 is collected.

The temperature of circulation water is then gradually increased up to 44.5° C., and is held at such value for the next 6 hours. At this time the bottom valve is opened once more, and the fraction 2 is collected. Finally, the temperature of water is raised, so as to melt the solid residue inside the tubes and to discharge the end product purified 2,6-xylenol.

In Table 3 the results are reported of the Example described above.

TABLE 3

| Fraction | Percentage by weight | 2,6-xylenol (% by weight) | o-cresol (% by weight) | m- & p-cresol (% by weight) | 2,4- & 2,5-xylenol (% by weight) | Solidification temper. (°C.) |
| --- | --- | --- | --- | --- | --- | --- |
| Raw material | 100 | 98.3 | 0.05 | 1.1 | 0.5 | 44.3 |
| Fraction 1 | 17 | 95.0 | 0.1 | 3.7 | 1.1 | 41.1 |
| Fraction 2 | 15 | 98.5 | 0.03 | 1.0 | 0.85 | 44.2 |
| End product | 68 | 99.9 | — | 0.1 | — | 45.3 |

We claim:

1. A process for purifying raw 2,6-xylenol, comprising:
(a) melting raw 2,6-xylenol without the addition of an aliphatic organic acid;
(b) cooling said molten raw 2,6-xylenol in a slow and uniform way, at a rate from 0.1° to 10° C./hour, until at least 60% to 100% of the mass is separated as a crystalline solid which is richer in impurities nearer the surface;
(c) gradually heating said crystalline solid, after having separated any liquid molten fraction, in a time from 1 to 12 hours, up to a maximum temperature of 0.1° to 5° C. lower than the solidification temperature of 2,6-xylenol, to cause melting on the surface of said crystals and to form a molten liquid fraction and a crystalline solid residue fraction, said molten liquid fraction being richer in impurities than said crystalline solid residue fraction; and (d) separating the molten liquid fraction and recovering the crystalline solid residue, which comprises purified solid 2,6-xylenol.

2. A process as claimed in claim 1, wherein the raw 2,6-xylenol starting material has a content of 2,6-xylenol of from about 95% to about 98%.

3. A process as claimed in claim 1, wherein in step (b) the cooling is carried out at a cooling rate of from 1° to 2° C./hour.

4. A process as claimed in claim 1, wherein in step (b) the cooling is carried out until about 80% of the charged batch is solidified.

5. A process as claimed in claim 1, wherein the molten liquid fraction which is formed in step (c) is collected continuously.

6. A process as claimed in claim 1, wherein the liquid molten fraction which is formed in step (c) is collected intermittently.

7. A process as claimed in claim 1, which is carried out in a tube nest crystallizer equipped with a heat exchange fluid externally to the same tubes.

* * * * *